United States Patent [19]

Saika

[11] Patent Number: 4,699,274
[45] Date of Patent: Oct. 13, 1987

[54] CLEANING DEVICE OF RAY TRANSMISSION WINDOW INCORPORATED INTO OPTICAL SELECTOR

[75] Inventor: Nobuo Saika, Wakayama, Japan

[73] Assignee: Toyo Seimaiki Seisakusho Kabushiki Kaisha, Wakayama, Japan

[21] Appl. No.: 832,243

[22] Filed: Feb. 24, 1986

[30] Foreign Application Priority Data

Mar. 7, 1985 [JP] Japan .................................. 60-45627

[51] Int. Cl.⁴ .......................... B07C 5/342; A47L 1/00
[52] U.S. Cl. .................................... 209/587; 15/250.1; 209/580
[58] Field of Search ............... 209/576, 577, 580, 587, 209/588, 639; 15/250.1, 256.5

[56] References Cited

U.S. PATENT DOCUMENTS

| 3,638,274 | 2/1972 | Farver | 15/250.10 |
| 3,859,688 | 1/1975 | Fiala | 15/250.10 |
| 4,074,808 | 2/1978 | Gillespie et al. | 209/587 |
| 4,426,005 | 1/1984 | Satake | 209/639 |

FOREIGN PATENT DOCUMENTS

| 898465 | 4/1972 | Canada | 15/250.10 |
| 56-137782 | 10/1981 | Japan . | |
| 2099141 | 12/1982 | United Kingdom | 209/580 |
| 2136955 | 9/1984 | United Kingdom | 209/580 |

Primary Examiner—David A. Scherbel
Assistant Examiner—Donald T. Hajec
Attorney, Agent, or Firm—Browdy and Neimark

[57] ABSTRACT

A cleaning device for a window used in an optical inspection device. The cleaning device removes dust which adheres to the transparent window by means of a dust scraper which contacts the surface of the window so as to enable the dust adhering to the surface of the window to be removed.

4 Claims, 6 Drawing Figures

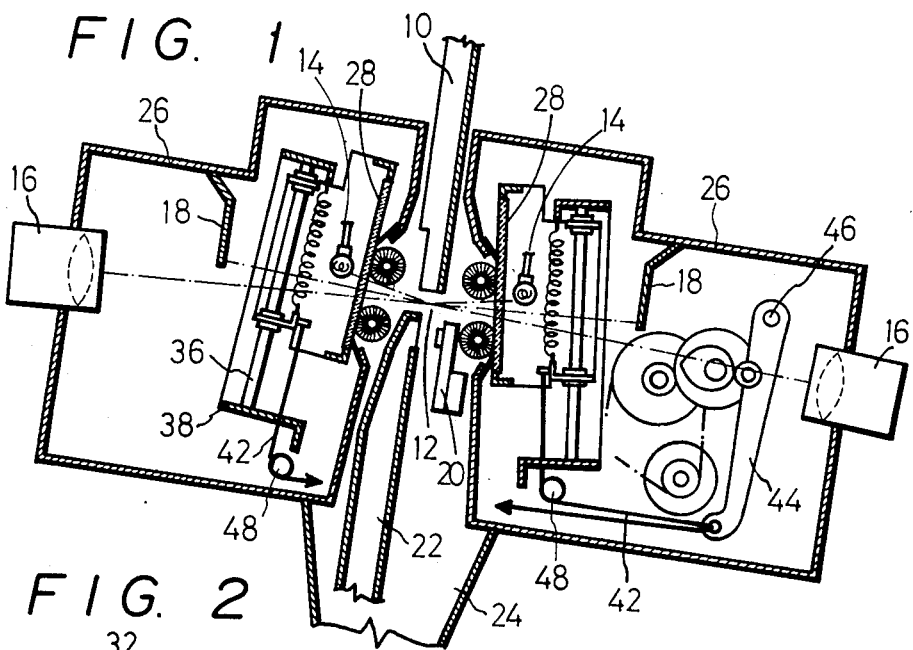
FIG. 1
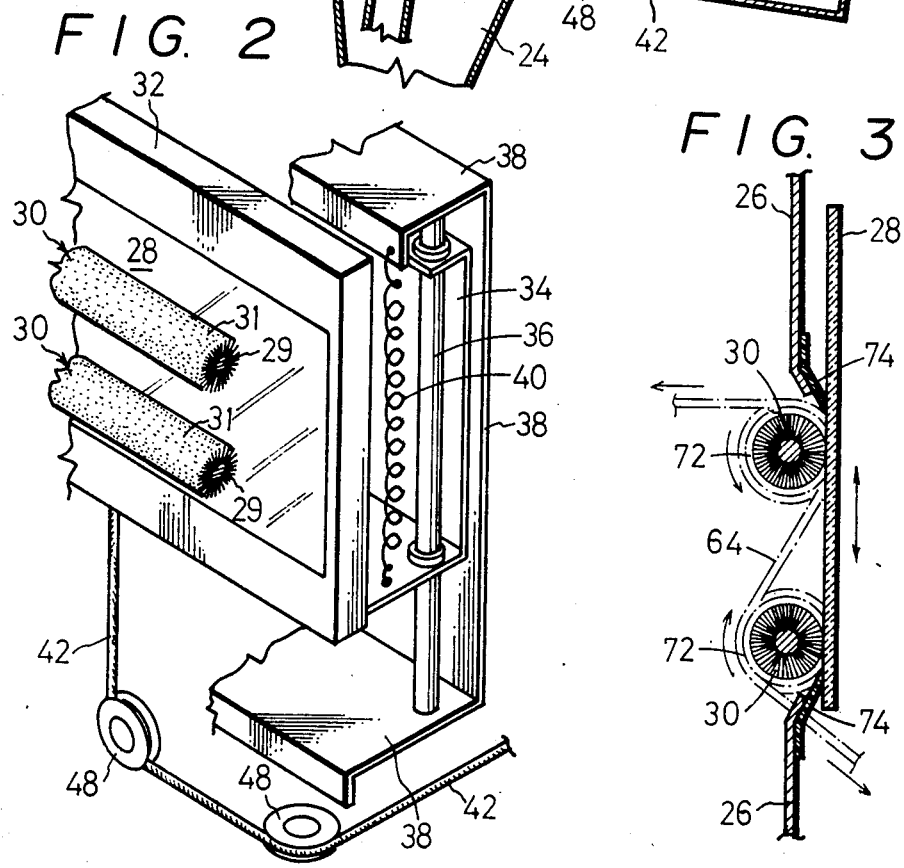
FIG. 2
FIG. 3

CLEANING DEVICE OF RAY TRANSMISSION WINDOW INCORPORATED INTO OPTICAL SELECTOR

FIELD OF THE INVENTION

The present invention relates to a device for cleaning windows on optical selection devices, such as are used in machines for selecting particulate agricultural products such as grains or beans, or particulate mineral or industrial products, depending upon the color of the surfaces of the objects.

BACKGROUND OF THE INVENTION

Generally, machines for optically selecting particulate articles such as agricultural products, wherein the selection depends upon the color of the surface of the article, are already in use. These selectors are structured so that the articles to be selected are dropped, a ray of light irradiates the article during the descent of the article, and the reflected or transmitted ray is measured to determine whether the article is to be selected. If the article is not selected, a blast of air is instantaneously applied to the article, thereby blowing off an abnormal particle in order to remove the same.

Since this selector performs the removal of particles by means of a blast of air, any fine dust which accompanies the article to be selected, such as sugar, particulate dust, and the like included in the grain, is blown up onto the machine. Although the space in which the selecting performance is executed is covered with a bulkhead so that dust does not adhere to various parts of the machine, the dust remains in the machine. The place through which the ray is transmitted is a transparent window, as the ray must irradiate the articles to be selected during their descent, and any dust that is blown up by the blast of air adheres to the window. If any dust adheres to the window, it obstructs the transmission of the ray, which interferes with the selection process. For this reason, it is necessary to provide a device for cleaning the dust which adheres to the window. Such a cleaning device has been proposed in the prior art. In the conventional cleaning device, a scraper such as used as a window wiper for an automobile is mounted to the surface of the window, and the scraper is adapted to be moved along the surface of the window at fixed intervals to eliminate any dust adhering to the window. Nevertheless, the conventional cleaning device has a defect in that the ray is interrupted when the scraper is moved. For this reason, the selecting work cannot be performed during the cleaning process, so that the selecting machine must be stopped whenever the cleaning work is performed. For this reason, the conventional selectors have an extremely low work efficiency.

SUMMARY OF THE INVENTION

The primary object of the present invention is to provide a cleaning device which is simple in structure and low in production cost, which is used along a ray transmission window of an optical selector.

Another object of the present invention is to provide a cleaning device which is capable of eliminating, fully and efficiently, the dust which adheres to the surface of a ray transmission window.

A further object of the present invention is to provide a device capable of cleaning a window without an interruption of the operation of the selector.

A still further object of the present invention is to provide a cleaning device capable of performing the cleaning work of the window, not only intermittently at adequately fixed interval, but also continuously.

A still further object of the invention is to provide a device capable of cleaning a window without obstructing optical inspection by eliminating the dust from the window.

BRIEF DESCRIPTION OF THE DRAWINGS

Other characteristics and advantages of the present invention will be apparent from the under mentioned description made in conjunction with the accompanying drawings.

FIG. 1 is a sectional view of the overall outline of the mechanism of an optical selector into which one preferred embodiment of a cleaning device according to the present invention is incorporated;

FIG. 2 is a perspective view illustrating partially the ray transmission window of the embodiment of FIG. 1;

FIG. 3 is a sectional view of a part of the window of the embodiment of FIG. 1;

FIGS. 5 and 6 are side views of other embodiments of the scraper, in which FIG. 5 illustrates a descent of the window, while FIG. 6 illustrates an ascent of the window.

DETAILED DESCRIPTION OF THE PREFERRED EMBODIMENT

Figure 4:
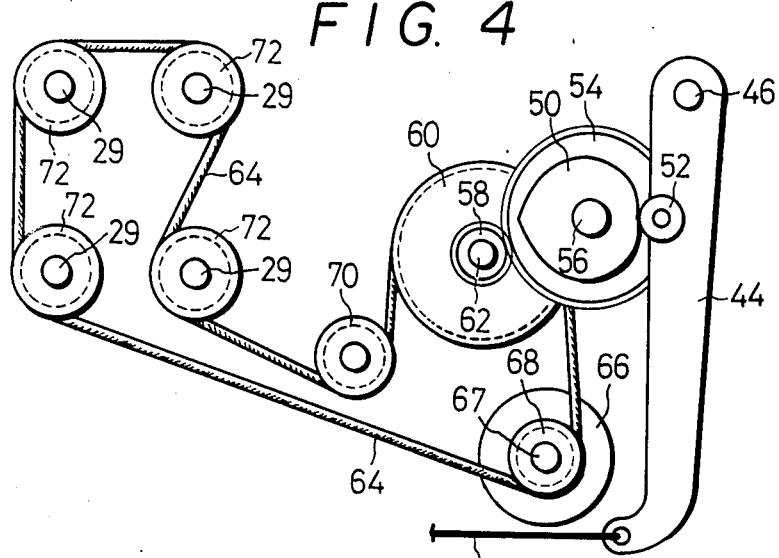
FIG. 4 is a side view of the drive mechanism for vertically moving the window.

An outline of the optical selector in which one embodiment of the cleaning device according to the present invention is incorporated is illustrated by FIG. 1. First of all, a description of the structure and the actuation of the optical selector is given. Particulate articles are supplied to the upper end of a chute 10. These articles flow down along the surface of the chute 10 due to their tare weight, and, by being accelerated at a predetermined velocity, they shoot out of the lower end of chute 10. Chute 10, being relatively wide, is divided into several compartments by equally spaced bulkheads which extend down each of the compartments. An inspection point 12 is located just under the lower end of chute 10. When the particulate articles pass the inspection point 12, lamps 14 provided on both sides of the chute apply rays to the particulate articles. If the articles are translucent, the ray is partially transmitted. If, for example, polished rice is used for the particulate articles, it is slightly translucent, for it transmits a partial portion of the incident ray. The light which is reflected from the surface of the particulate articles and other transmitted light reach sensors 16 provided on both sides of the optical selector. The light from the lamps 14 on both the sides impinges on backscreens 18 respectively provided on both sides and the light which is reflected from backscreens 18 reaches sensors 16. The quantity of light reflected from backscreens 18 is set to coincide with the quantity of light reflected from the normal particulate articles, including the quantity of transmitted light for the extraordinary case. Sensors 16 inspect as to whether the quantity of light from the particulate articles is identical to the quantity of light from backscreens 18. If there is any abnormality in the color of the surface of the particulate article, it gives rise to a difference in the quantity of light, whereby sensor 16 detects an existence of an abnormal particulate article. A signal signifying discovery of an abnormal particulate article is fed from the sensors 16 to air injection equipment 20, which instantaneously blows high pressure air against the abnormal particulate article, thereby blowing it away. The air injection equipment is positioned so as to be slightly lower than the inspection point 12 because of the time lag necessary for a commencement of the actuation of the air injection equipment 20. When the particulate article which is judged to be abnormal at inspection point 12 falls down to the position of the air injection equipment 20, air is expelled from equipment 20. As mentioned above, since chute 10 is divided into several compartments, and the particulate articles are adapted to fall down each of the compartments, both the inspection of the quantity of light and the selection of the particulate articles by the use of expelled air is performed individually for each of the compartments. Thus, upon the discovery of an abnormal particulate article, a simultaneous expulsion of air blows away the particulate article so that is enters into a receiving part 22 for the abnormal particulate article. Normal particulate articles do not receive the expelled air blast, and fall straight down so that they enter into another receiving part 24 for normal particulate articles. If the normal particulate articles are moving in close formation to an abnormal particulate article, the air expulsion, which is effected within the range of an extremely small area, may sometimes blow off the abnormal particulate articles together with normal particulate articles. For this reason, an arrangement is also possible in which the particulate articles collected in receiving part 22 for abnormal particulate articles are again put through a selection process to eliminate only the abnormal particulate articles.

The dust blown up by the blast of wind is adapted not to adhere to members of the machine such as lamps 14 and backscreens 18, which are housed in the dust protective cabinet 26. Cabinet 26 possesses a transparent window 28 at its opening through which the ray is transmitted. Window 28 is movable in a vertical direction. Rotating brushes 30 move into contact with the surface of windows 28. The rotating brushes 30 have a multiplicity of brush hairs 31 planted radially around shafts 29 respectively which are rotatably supported at fixed positions. Any convenient brush hair design can be used, such as partial or full coverage, or, for example, a helical design using brush hairs 31. Rotating brush 30 is rotated around a fixed axis, and does not move together with a vertical motion of window 28. Nevertheless, despite the vertical motion of window 28, rotating brush 30 remains in contact with the surface of window 28. Two rotating brushes 30 are arranged vertically and separately in two such positions along both windows 28 respectively so that they do not obstruct the transmission of the light rays. If rotating brushes 30 are rotated and windows 28 are moved, the dust which adheres to window 28 is eliminated. While it may be acceptable to perform the cleaning work intermittently at the adequately fixed intervals which take into account normal accumulation of dust, such as intervals of 10 or 20 minutes, the cleaning may also be effected continuously.

A supporting and a driving means for window 28 and a driving means for rotating brushes 30 are illustrated in FIGS. 2, 3, and 4. The edges of transparent window 28 are fixed by a frame 32. Frame 32 has a supporting member 34, which is slidably connected to a guide rod 36. Guide rod 36, which is fixed to a fixing member 38, does not move. A spring 40 which is disposed between fixing member 38 and supporting member 34 is attached to lift up window 28. Wires 42 for pulling down windows 28 are connected to both frames 32, respectively, around both windows 28. When pulling one wire 42, window 28 is moved down along guide rod 36. When wire 42 is loosened, window 28 is returned upward by the force of spring 40. The other end of wire 42 is connected to the end of a lever 44. When lever 44 is moved with shaft 46 as a fulcrum, wire 42 is either pulled out or loosened. Wire 42 is led by way of guide wheels 48 provided in adequate positions in the path from lever 44 to frame 32. The motion of lever 44 is controlled by a cam 50. Rotation of cam 50 is followed by a movement of lever 44. Cam 50, which is mounted on shaft 56 onto which a gear 54 is mounted, is integrally rotated when gear 54 is rotated. When another gear 58 which is in mesh with gear 54 is rotated, gear 54 is rotated. Gear 58 is mounted on shaft 62, which is the same shaft on which guide wheel 60 is mounted, and both gear 58 and wheel 60 are rotated together. An endless transmission member 64 is wound around guide wheel 60. A chain or a belt is used as the endless transmission member 64. In the case of using a chain, a sprocket serves as the guide wheel 60, while, in the case of a belt, a pulley is used for that purpose. The endless transmission member 64 is also wound around guide wheel 68 mounted on shaft 67 of a motor 66. For this reason, when the motor 66 moves, endless transmission member 64 is moved, and guide wheel 60 is rotated. Endless transmission member 64 is wound by way of guide wheel 70 disposed as needed and also around guide wheels 72, each mounted respectively on a shaft 29 of one of the rotating brushes 30. For this reason, upon movement of endless transmission member 64, all of the rotating brushes 30 are rotated at the same time. The edges of the window openings of the cabinet 26 are equipped with elastic shielding materials 74, the top ends of which are held in contact with the surface of the window, preventing dust form being forced into then inside by means of the gap between the end of the window opening and the window 28.

A description of the actuation of the device is as follows. If the particulate articles to be selected, such as grain, are supplied at the upper end of chute 10, they fall down, sliding along the surface of chute 10, and are accelerated at an adequate velocity after which they drop out of the lower end of chute 10. When the particulate articles reach the inspection point 12, rays from lamps 14 impinge upon their back and front surfaces. The light which is reflected from the particulate articles reaches sensors 16 provided on both sides of cabinet 26. If the particulate articles are translucent, the transmitted light is added to the reflected light. A comparison between the light from them and the light which is reflected on the backscreens 18 is made. Since the quantity of the light which is reflected on the backscreens 18 is set to coincide with the quantity of light from the abnormal articles, sensors 16 detect the presence of an abnormal article if there is a difference in the quantity of light from the backscreens and the articles. Since the quantity of the reflected light and the transmitted light from the particulate article having an abnormally colored surface is different from the quantity of light from the normally colored particulate articles, sensors 16 can easily discover the abnormal particulate articles. The signal indicating detection of the abnormal particulate article is fed from sensors 16 to air injection equipment 20, and high pressure air is instantaneously blasted. During blasting of the air, the particulate articles fall down to the front face of the air injection equipment 20, so that the blast of air blows at the particulate articles, which fly into receiving part 22. In the case of normal particulate articles, which are not detected by sensors 16, since they are not subjected to a blast of air, they fall straight down, entering into receiving part 24. Thus, the particulate article which has an abnormally colored surface is selected to be eliminated. Since the selecting and eliminating process is effected by the blast of air, the fine dust included in the articles to be selected is blown up and adheres to the surface of window 28. If the amount of dust adhering thereto is increased, transmission of the rays is obstructed, which impedes the selection process taking place. For this reason, at fixed intervals which take into account the amount of dust generated, e.g., approximately 10 minutes, the cleaning device is actuated. Usually, a timer is used for intermittently setting adequate intervals. The timer control intermittently drives motor 66. When motor 66 starts, endless transmission guide member 64 begins to move, and both rotating brushes 30 and guide wheel 60 are rotated at the same time. Rotation of guide wheel 60 is transmitted by way of gears 58 and 54 to cam 50, which, being rotated, reciprocates lever 44, and the wires 42 are adapted to be pulled out or loosened. As a result, when wire 42 is pulled out, both the windows 28 are moved downwardly, whereas when wire 42 is loosened, the windows 28 are returned upwardly by force of spring 40. When lever 44 is reciprocated once, window 28 is also vertically reciprocated once. When brush 30 is rotated, window 28 is concurrently moved vertically, so that the dust which adheres to the surface of window 28 is removed by the brush 30. In the usual case, since a reciprocal motion of window 28 may almost fully remove the dust, it is preferable that motor 66 is to be driven only during such a reciprocal motion thereof, and subsequently motor 66 is stopped. In the case where the amount of dust adhering to the window is considerably greater, it is also possible to drive the motor 66 during a plurality of reciprocal motions thereof, as continuous operation of motor 66 is permissible.

If the foregoing embodiment of the cleaning device according to the present invention, window 28 is moved vertically. A modification is possible in which window 28 may be moved laterally. If a curved window of semicircular shape is used, a semi-circular motion may be used.

Figure 5:
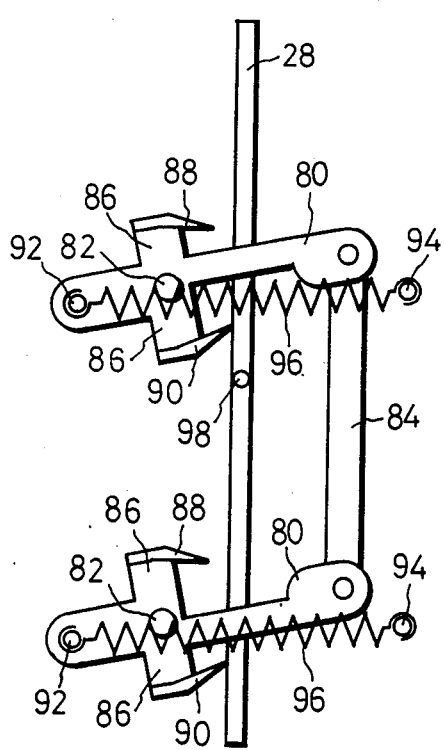
Figure 6:
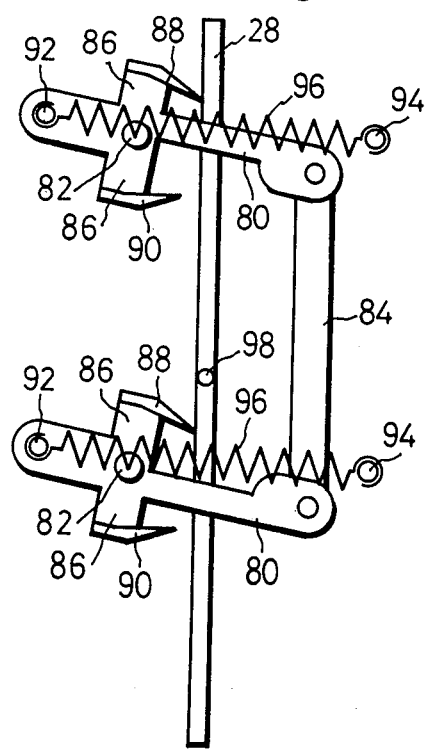

Referring now to FIGS. 5 and 6, illustrating yet another embodiment of the scraper, shaking members 80 are slidably supported by the shafts 82. Two shaking members 80 are slidably supported by the shafts 82. The two shaking members 80 are provided in the vertical direction, and both of them are connected to each other by a connecting rod 84. For this reason, the upper and lower shaking members 80 are always integrally moved together. The upper and lower sides of the shaking members 80 possess arms 86, to which scraping pieces 88 and 90 are mounted. These scraping pieces 88 and 90 are elastic and can be made of rubber. Shaking members 80 are provided respectively on both sides of window 28, and scraping pieces 88 and 90 form a bridge between shaking members 80 on both sides. Springs 96 are stretched between pins 92 of the shaking members 80 and fixed pins 94. When window 28 reaches its uppermost position or its lowermost position, a projection 98 which is mounted on the side edge of window 28 makes contact with shaking members 80, thereby pushing shaking members 80 in an opposite direction. That is, when window 28 reaches its uppermost position, projection 98 makes contact with the upper shaking member 80, whereby shaking members 80 are moved into the position shown in FIG. 5. The projection 98 therefore serves as means for shaking the shaking member. In this position, the top end of lower scraping piece 90 comes into contact with the surface of window 28. Furthermore, such a position is held by the tensile force of spring 96, where even the beginning of a descent of window 28 is unable to release scraping piece 90 from its position. As a result, the dust which adheres to the surface of window 28 is eliminated by scraping piece 90. When window 28 moves a second time and reaches its lowermost position, the projection 98 pushes the lower shaking member 80, thereby moving shaking member 80 into such a position as shown in FIG. 6. At that time, the upper scraping piece 88 moves to make contact with the surface of window 28. When window 28 ascends, the dust which adheres to the surface of window 28 is removed therefrom. Thus, by making a shift in using the upper and lower scraping pieces 88 and 90, no mass of dust is left on the surface of the window 28 through the complete cleaning cycle. Namely, when window 28 descends, the dust which adheres thereto is scraped off by scraping piece 90, but some portions of the scraped dust which are left as a mass on the top end of the scraping piece 90 remain on the surface of window 28, when window 28 ascends from its lowest position. If such a mass of dust is left on the surface of window 28, it obstructs the transmission of the light rays. Nevertheless, as mentioned above, since shaking member 80 makes a change to the opposite side and the upper scraping piece 88 turns to make contact with the surface of window 28, a mass of remaining dust is removed by scraping piece 88.

What is claimed is:

1. In an optical selector wherein articles are conveyed downwardly past an optical selection means, light rays transmitted through a window impinge on the articles as they are moving downwardly, detecting the quantity of light reflected by the article, comparing the quantity of light reflected with a quantity of light reflected by a standard article, and using a blast of air to remove an article which is not selected, the improvement comprising a cleaning device for the window, said cleaning device comprising:

a dust preventing cabinet having an opening through which said light rays are transmitted;

a transparent window movably mounted over said opening of said dust prevention cabinet, said window having an upper part and a lower part;

means for moving said window in a direction parallel to the surface plane of said window, said moving means connected to said window;

a dust scraper in a fixed position so as to be in constant contact with a surface of said window;

a linear guide supporting said window and along which said window is moved linearly;

a fixing member to which said linear guide is fixed;

a spring disposed between said fixing member and said window, and a pulling-out means connected to said window for providing a pulling force to move said window downwardly along said guide, said window being moved upwardly under the force of said spring.

2. The cleaning device of claim 1 wherein said dust scraper includes rotating brushes mounted in a fixed position.

3. The cleaning device of claim 1 wherein said dust scraper further includes elastic scraping pieces which are detachably in contact with said window, said scraping pieces being mounted on shaking members, said window including means for shaking said shaking members, said shaking members having a first side and a second side, each side provided with one of said scraping pieces, the first side and the second side in an arrangement such that when said window is moved, the scraping piece on the first side of said shaking member is positioned into contact with the surface of said window, and when said window is moved a second time, said scraping piece positioned at said second side of said shaking member moves into contact with the surface of said window.

4. The cleaning device of claim 3 wherein said shaking members carrying two said scraping pieces are provided on upper and lower parts of said window respectively, said shaking members connected to each other at upper and lower parts thereof and adapted to be integrally shaken, and said means for shaking including a projection mounted on the side edge of said window contacting said shaking members in order to shift the position of said shaking members.

* * * * *